US00PP24719P3

(12) United States Plant Patent

Klemm et al.

(10) Patent No.: US PP24,719 P3

(45) Date of Patent: Jul. 29, 2014

(54) *BIDENS* PLANT NAMED 'KLEBF11764'

(50) Latin Name: *Bidens ferulifolia*
Varietal Denomination: KLEBF11764

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 68 days.

(21) Appl. No.: 13/506,063

(22) Filed: Mar. 23, 2012

(65) Prior Publication Data

US 2013/0254960 P1 Sep. 26, 2013

(51) Int. Cl.
*A01H 5/00* (2006.01)

(52) U.S. Cl.
USPC ..... Plt./410

(58) Field of Classification Search
CPC ..... A01H 5/025
USPC ..... Plt./410
See application file for complete search history.

(56) References Cited

U.S. PATENT DOCUMENTS

PP20,533 P3 * 12/2009 Klemm ..... Plt./410

* cited by examiner

*Primary Examiner* — June Hwu
(74) *Attorney, Agent, or Firm* — Jondle Plant Sciences Division of Swanson & Bratschun, L.L.C.

(57) ABSTRACT

A new variety of *Bidens* plant named 'KLEBF11764' particularly characterized by early and rich flowering with inflorescences situated above the plant center and short peduncles is disclosed.

1 Drawing Sheet

Genus and species: *Bidens ferulifolia*.
Variety denomination: 'KLEBF11764'.

BACKGROUND OF THE NEW PLANT

The present invention comprises a new and distinct variety of *Bidens*, botanically known as *Bidens ferulifolia*, and hereinafter referred to by the variety name 'KLEBF11764'. 'KLEBF11764' resulted from an open pollination between July and September of 2007 in Stuttgart, Germany between the female parent *Bidens* plant 'BF 07 0011' (unpatented) and an unknown male parent. A single plant selection was subsequently chosen for further evaluation and asexual propagation.

The new variety was first propagated via vegetative cuttings and in vitro propagation in May 2008 in Stuttgart, Germany and has been asexually reproduced repeatedly by vegetative cuttings in Stuttgart, Germany for 12 generations. 'KLEBF11764' has been found to retain its distinctive characteristics through successive asexual propagations.

Plant Breeder's Rights for this variety have not been applied for. 'KLEBF11764' has not been made publicly available more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. Early and richly flowering;
2. Flowers situated above the plant centers; and
3. Short peduncles.

DESCRIPTION OF THE PHOTOGRAPH

This new *Bidens* plant is illustrated by the accompanying photograph which shows flowers of the plant. The colors shown are as true as can be reasonably obtained by conventional photographic procedures. The photograph was taken on a plant about 3 months old grown from rooted cuttings in a 10 centimeter pot in a glass greenhouse in Stuttgart, Germany under normal horticultural practices.

DESCRIPTION OF THE NEW VARIETY

The following detailed descriptions set forth the distinctive characteristics of 'KLEBF11764'. The data which define these characteristics were collected from asexual reproductions carried out in Stuttgart, Germany. The plant history was taken in spring 2011 on 10 week old plants grown in 10 centimeter pots in a glass greenhouse with a minimum pinch date of 9 weeks. The color readings were determined under natural light. Color references are to The R.H.S. Colour Chart of The Royal Horticultural Society of London (R.H.S.), Fifth Edition (2007).

DESCRIPTION OF THE NEW PLANT

Classification:
- *Family*.—Asteraceae.
- *Genus and species*.—*Bidens ferulifolia*.
- *Common names*.—*Bidens*, Beggarticks, Bur-marigold, tickseed.
- *Denomination*.—'KLEBF11764'.

Parentage:
- *Female parent*.—*Bidens* plant 'BF 07 0011'.
- *Male parent*.—Unknown.

Plant:
- *Propagation*.—Vegetative cuttings.
- *Time to initiate and develop roots*.—2 weeks.
- *Root description*.—Fine white roots, RHS N155C.
- *Rooting habit*.—Freely branching.

*Appearance and type*.—Round to flat.
*Habit*.—Half hanging.
*Height* (*from top of soil*).—8.0 cm.
*Diameter* (*plant spread*).—11.0 cm.

Branches:
*Lateral branches* (*quantity per plant*).—5 to 6.
*Length*.—6.0 cm to 10.0 cm.
*Diameter*.—0.2 cm.
*Internode length*.—1.0 cm to 3.0 cm.
*Texture*.—Pubescent.
*Color*.—RHS 143C with brownish/reddish stripes between RHS 178A and 177D.

Leaves:
*Arrangement*.—Opposite.
*Shape*.—Ovate.
*Apex*.—Obtuse.
*Base*.—Acute.
*Margin*.—Pinnate.
*Texture* (*both surfaces*).—Smooth.
*Length*.—4.0 cm.
*Width*.—3.0 cm to 4.0 cm.
*Color*.—Immature leaf: Upper surface: RHS 143A. Lower surface: RHS 139C. Mature leaf: Upper surface: RHS 141A. Lower surface: RHS 139C.
*Venation pattern*.—Pinnate.
*Venation color*.—RHS 144D.
*Petioles*.—Length: 1.5 cm to 2.0 cm. Diameter: Less than 0.1 cm. Texture: Pubescent. Color: RHS 143C.

Inflorescence:
*Appearance*.—Daisy-type.
*Diameter*.—3.5 cm to 4.5 cm.
*Depth*.—0.5 cm to 0.7 cm.
*Diameter of disc*.—0.8 cm to 1.0 cm.
*Number of inflorescences and buds per plant*.—5 to 15.
*Lastingness of individual blooms on the plant*.—3 to 4 days.
*Fragrance*.—Present.

Bud:
*Length*.—0.5 cm to 0.7 cm.
*Diameter*.—0.4 cm.
*Shape*.—Cylindric.
*Color*.—RHS 199A (Brownish) and RHS 1B (Yellow).

Ray florets:
*Length*.—2.0 cm to 2.5 cm.
*Width*.—1.0 cm to 1.2 cm.
*Shape*.—Ovate.
*Apex*.—Tridentate.
*Base*.—Acute.
*Margin*.—Entire.
*Texture* (*both surfaces*).—Smooth.
*Number of ray florets per inflorescence*.—5-8.
*Color* (*when opening*).—Upper surface: RHS 9A. Lower surface: RHS 8A.
*Color* (*when fully opened*).—Upper surface: RHS 9A. Lower surface: RHS 8A with dark colored stripes of RHS 199B.

Disc florets:
*Shape*.—Tubular.
*Apex*.—Five-pointed.
*Base*.—Fused.
*Margin*.—Entire.
*Number of disc florets per inflorescence*.—40 to 60.
*Length*.—0.6 cm to 0.7 cm.
*Diameter*.—0.1 cm.
*Color*.—RHS 1C.

Phyllaries:
*Quantity and color*.—8 green and 6 yellow.
*Length* (*irregular*).—0.2 cm to 0.4 cm.
*Width*.—0.1 cm.
*Shape*.—Lanceolate.
*Apex*.—Acute.
*Base*.—Truncate.
*Margin*.—Entire.
*Texture* (*both surfaces*).—Smooth.
*Color of green phyllaries*.—Upper surface: RHS 143A. Lower surface: RHS 139C.
*Color of yellow phyllaries*.—Yellow phyllaries have a greenish base (RHS 154B). The color of the base also extends towards the margins. In between the base and margins there is a transition to yellow (RHS 8A) and at the tips there is a brownish region (RHS N200A).

Peduncles:
*Length*.—4.0 cm to 6.0 cm.
*Diameter*.—0.1 cm.
*Texture*.—Pubescent.
*Color*.—RHS 143C.

Reproductive organs:
*Androecium*.—Present on disc florets only. Stamen quantity: 5. Anther length: 0.1 cm to 0.15 cm. Anther color: RHS 200A. Pollen amount: Sparse to moderate. Pollen color: RHS 13A.
*Gynoecium*.—Present on disc florets only. Quantity per disc floret: 1. Pistil length: 0.3 cm. Stigma shape: Divided in 2 parts with long branches. Stigma length: 0.1 cm (depth)/0.4 cm (length added from both parts). Stigma diameter: 0.2 cm. Stigma color: RHS 21A. Style length: 0.2 cm. Style color: RHS 20C.

Fruit and seed set: None observed.

Disease and insect resistance: No particular disease or insect resistance observed.

COMPARISON WITH PARENTAL AND COMMERCIAL VARIETIES

'KLEBF11764' differs from the female parent, *Bidens* plant 'BF 07 0011' (unpatented), in that 'KLEBF11764' is a richer flowering variety and has shorter peduncles.

'KLEBF11764' differs from commercial variety 'KLEBF07003' (U.S. Plant Pat. No. 20,533) in that 'KLEBF11764' has an upright/semi-trailing habit, whereas 'KLEBF07003' has a trailing habit. In addition, 'KLEBF11764' initiates and develops roots in 2 weeks, whereas 'KLEBF07003' initiates and develops roots in 3 weeks.

We claim:

1. A new and distinct variety of *Bidens* plant named 'KLEBF11764' as shown and described herein.

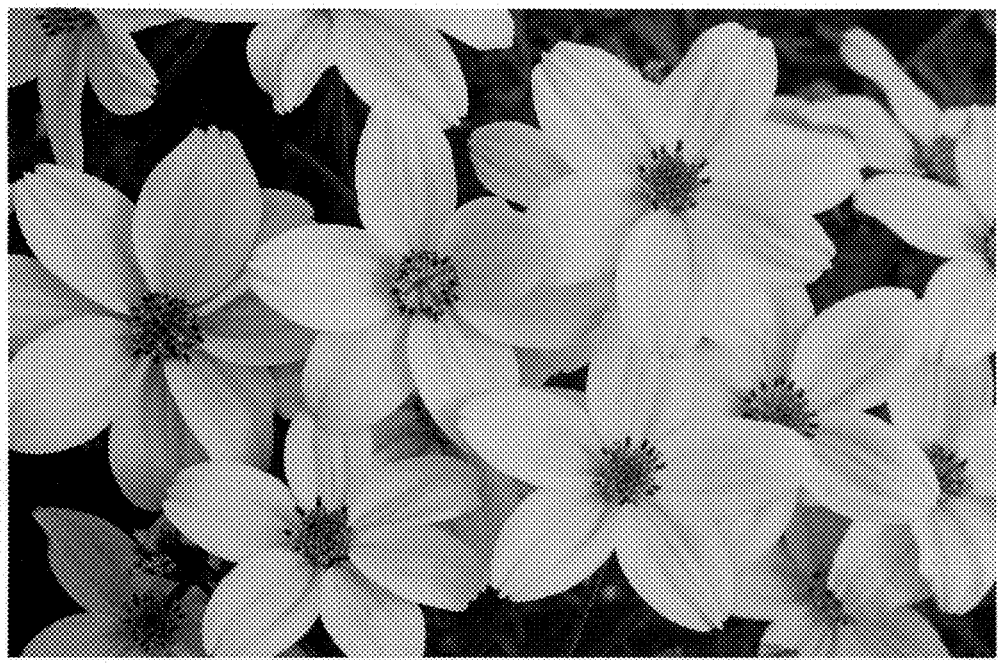

* * * * *